United States Patent [19]

Kirst

[11] 4,379,917

[45] Apr. 12, 1983

[54] 6"-(SUBSTITUTED)-APRAMYCIN ANTIBIOTIC DERIVATIVES AND INTERMEDIATES AND STARTING MATERIALS THEREFOR

[75] Inventor: Herbert A. Kirst, Indianapolis, Ind.

[73] Assignee: Eli Lilly and Company, Indianapolis, Ind.

[21] Appl. No.: 334,409

[22] Filed: Dec. 24, 1981

[51] Int. Cl.$^3$ .............................................. C07H 15/22
[52] U.S. Cl. .................................... 536/16.8; 424/180
[58] Field of Search ................... 536/4, 17 R, 16.8; 424/118

[56] References Cited

U.S. PATENT DOCUMENTS 3,691,279  9/1972  Thompson et al. ................. 424/118
3,853,709 12/1974  Stark ................................... 424/118
3,876,767  4/1975  Ose ..................................... 424/118

OTHER PUBLICATIONS

O'Connor et al., "Chem. Abst.", vol. 85, 1976, p. 21760(t).
Abe et al., "The Jour. of Antibiotics", vol. XIV, 1981, pp. 1434-1443.
T. Miyasaka et al., *J. Antibiotics (Tokyo)*, 33, 527 (1980).
T. L. Nagabhushan and P. J. L. Daniels, *J. Med. Chem.*, 17, 1030 (1974).
H. Umezawa et al., *J. Antibiotics (Tokyo)*, 25, 743 (1972).
S. Toda et al., *J. Antibiotics (Tokyo)*, 30, 1002 (1977).
S. Inouye, *J. Antibiotics (Tokyo) Ser. A.*, 20, 6 (1967).
T. Tsuchiya and S. Umezawa, *Bull. Chem. Soc. Jap.*, 38, 1181 (1965).
Y. Abe et al., *J. Antibiotics (Tokyo)*, 34, 1434 (1981).
S. O'Connor et al., *J. Org. Chem.*, 41, 2087 (1976).
G. Kavadias et al., *Can. J. Chem.*, 56, 2086 (1978).
S. Hanessian et al., *Can. J. Chem.*, 56, 1500 (1978).
S. Umezawa et al., *J. Antibiotics* (Tokyo) *Ser. A.*, 20, 53 (1967).

*Primary Examiner*—Johnnie R. Brown
*Attorney, Agent, or Firm*—Paul C. Steinhardt; Nancy J. Harrison; Arthur R. Whale

[57] ABSTRACT

Apramycin derivatives substituted at the 6"-position with a variety of substituents are claimed as broad spectrum antibiotics. Also claimed are starting materials and intermediates in the synthesis of the above apramycin derivatives.

39 Claims, No Drawings

6"-(SUBSTITUTED)-APRAMYCIN ANTIBIOTIC DERIVATIVES AND INTERMEDIATES AND STARTING MATERIALS THEREFOR

BACKGROUND OF THE INVENTION

This invention relates to antibiotic derivatives of apramycin and intermediates and starting materials in the synthesis therefor. In particular, it relates to antibiotic derivatives of apramycin wherein the 6"-hydroxyl group is replaced by hydrogen, $C_1$ to $C_3$-alkylsulfonyloxy, phenylsulfonyloxy, substituted phenylsulfonyloxy, tert-butyldimethylsilyloxy, fluoro, chloro, bromo, iodo, azido, amino, $C_1$ to $C_3$-alkylthio, phenylthio, cyano or aminomethyl.

Apramycin is used as a veterinary antibiotic (see U.S. Pat. Nos. 3,691,279, 3,853,709 and 3,876,767) and has the following structure:

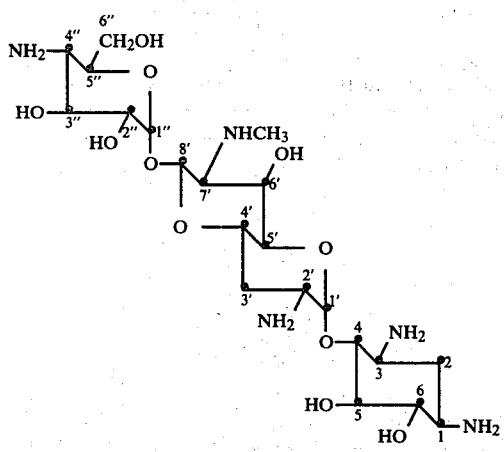

It is known in the aminoglycoside art that substitution on various positions of the aminoglycoside rings may increase the activity of the parent aminoglycoside. Some recent substituted-apramycin derivatives, in which the 1, 3 and 2'-amino groups were functionalized, have been reported by Herbert A. Kirst, Brenda A. Truedell and John E. Toth in Tetrahedron Letters, vol. 22, pp 295–298 (1981).

The apramycin derivatives of the instant application are substituted at the 6"-position as specified and possess broad-spectrum antibiotic activity while differing in structure from the aforementioned compounds and other compounds previously disclosed in the art.

SUMMARY OF THE INVENTION

The 6"-(substituted)apramycin antibiotics of this invention are represented by formula A:

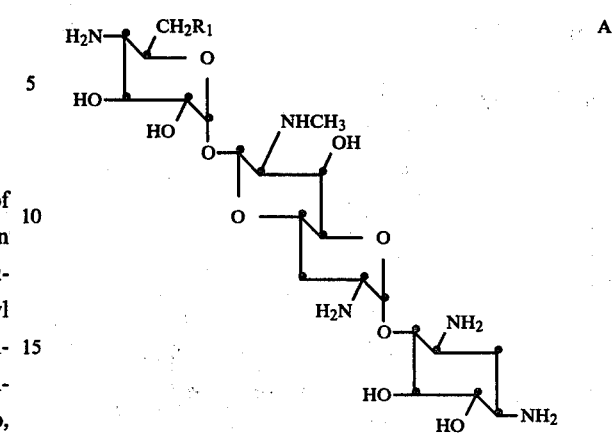

wherein $R_1$ is hydrogen, $C_1$ to $C_3$-alkylsulfonyloxy, phenylsulfonyloxy, substituted phenylsulfonyloxy, tert-butyldimethylsilyloxy, fluoro, chloro, bromo, iodo, azido, amino, $C_1$ to $C_3$-alkylthio, phenylthio, cyano or aminomethyl and the pharmaceutically acceptable acid addition salts thereof.

A second aspect of this invention are the intermediates in the synthesis of the above apramycin antibiotics. One group of intermediates is represented by formula B:

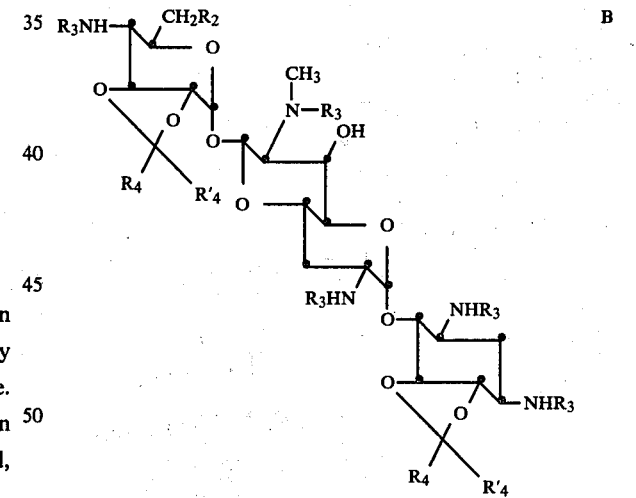

wherein $R_2$ is $C_1$ to $C_3$-alkylsulfonyloxy, phenylsulfonyloxy, substituted phenylsulfonyloxy, azido, fluoro, bromo, iodo, $C_1$ to $C_3$-alkylthio, phenylthio or cyano, $R_3$ is benzyloxycarbonyl, $C_1$ to $C_4$ alkoxycarbonyl, trichloroethoxycarbonyl, formyl, trifluoroacetyl or phenoxycarbonyl and $R_4$ and $R_4'$ are both methyl, or, taken together form a cyclohexyl ring.

The second group of intermediates in the synthesis of the above 6"-substituted apramycin antibiotics is represented by the following formula C:

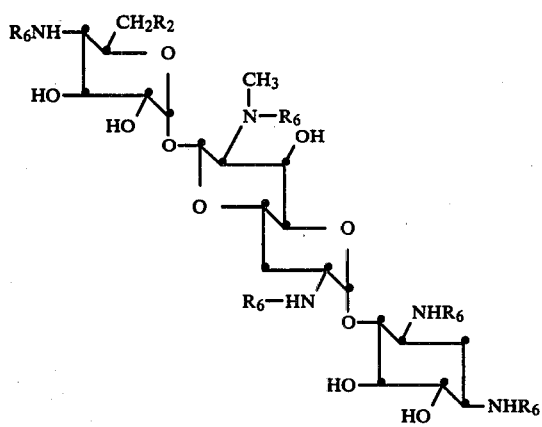

wherein $R_5$ is fluoro, chloro, bromo, iodo, cyano, $C_1$ to $C_3$-alkylsulfonyloxy, phenylsulfonyloxy, substituted phenylsulfonyloxy, azido, $C_1$ to $C_3$-alkylthio, phenylthio or tert-butyldimethylsilyloxy; and $R_6$ is benzyloxycarbonyl, $C_1$ to $C_4$-alkoxycarbonyl, trichloroethoxycarbonyl, formyl, trifluoroacetyl or phenoxycarbonyl.

A third aspect of this invention involves starting materials for the synthesis of the above intermediates. One group of starting materials is represented by the following formula D:

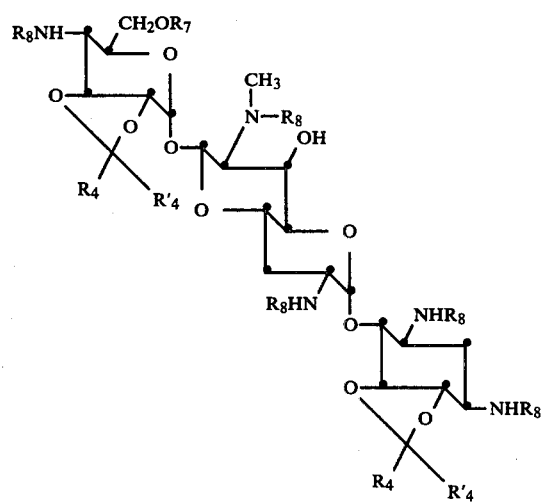

wherein $R_4$ and $R_4'$ are the same and are methyl or are taken together to form a cyclohexyl ring, $R_7$ is chosen from the group consisting of hydrogen, a substituent of the formula

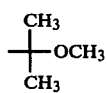

or a substituent of the formula

and $R_8$ is chosen from the group consisting of benzyloxycarbonyl, $C_1$ to $C_4$-alkoxycarbonyl, trichloroethoxycarbonyl, formyl, trifluoroacetyl or phenoxycarbonyl; provided that, when $R_7$ is a substituent of the formula

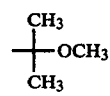

$R_4$ and $R_4'$ are methyl, and that, when $R_7$ is a substituent of the formula

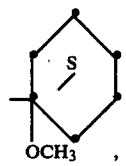

$R_4$ and $R_4'$ are taken together to form a cyclohexyl ring; and further provided that, when $R_4$ and $R_4'$ are taken together to form a cyclohexyl ring and $R_7$ is hydrogen or a substituent of the formula

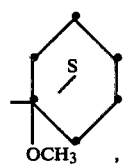

$R_8$ is other than ethoxycarbonyl.

The other group of starting materials is represented by formula E:

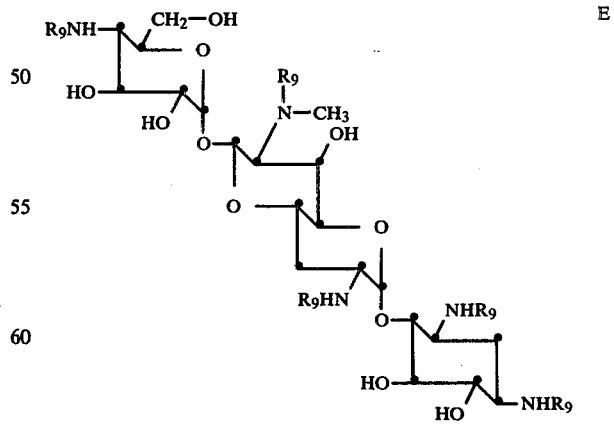

wherein $R_9$ is benzyloxycarbonyl, methoxycarbonyl, n-propoxycarbonyl, iso-propoxycarbonyl, n-butoxycarbonyl, tert-butoxycarbonyl, trichloroethoxycarbonyl, formyl, trifluoroacetyl or phenoxycarbonyl.

DETAILED DESCRIPTION OF THE INVENTION

This invention is directed to certain 6"-substituted-apramycin antibiotic compounds and the intermediates and the starting materials for the synthesis of these antibiotics.

Specifically, the apramycin antibiotics compounds claimed in this invention are substituted at the 6"-position with a substituent chosen from the group consisting of hydrogen, $C_1$ to $C_3$-alkylsulfonyloxy, phenylsulfonyloxy, substituted phenylsulfonyloxy, tert-butyldimethylsilyloxy, fluoro, chloro, bromo, iodo, azido, amino, $C_1$ to $C_3$-alkylthio, phenylthio, cyano or aminomethyl, and the pharmaceutically acceptable acid addition salts thereof.

Two groups of intermediates used in the synthesis of the 6"-substituted-apramycin antibiotic compounds are provided in this application. In the first group of intermediates, the 1,3,2',7' and 4"-amino groups are protected with a protecting group chosen from the group consisting of benzyloxycarbonyl, formyl, trifluoroacetyl, phenoxycarbonyl, $C_1$ to $C_4$-alkoxycarbonyl, and trichloroethoxycarbonyl, the 2",3" and 5,6 pairs of hydroxyl groups are each protected with an isopropylidene or cyclohexylidene group and the 6"-carbon is substituted with a substituent chosen from the group consisting of $C_1$ to $C_3$-alkylsulfonyloxy, phenylsulfonyloxy, substituted phenylsulfonyloxy, azido, fluoro, bromo, iodo, $C_1$ to $C_3$-alkylthio, phenylthio or cyano.

In the second group of intermediate compounds provided in the instant application, the 1,3,2',7', and 4"-amino groups are protected with same amino protecting groups as in the first group of intermediates, but the 2",3" and the 5,6 pairs of hydroxyl groups are not protected, while the substituent at the 6"-carbon is chosen from the group consisting of fluoro, chloro, bromo, iodo, $C_1$ to $C_3$-alkylsulfonyloxy, phenylsulfonyloxy, substituted phenylsulfonyloxy, azido, $C_1$ to $C_3$-alkylthio, phenylthio, cyano, and tert-butyldimethylsilyloxy.

Also provided in the instant application are two groups of starting materials. The first group of starting materials are apramycin derivatives wherein the 1,3,2',7' and 4"-amino groups are protected with a protecting group chosen from benzyloxycarbonyl, methoxycarbonyl, n-propoxycarbonyl, iso-propoxycarbonyl, n-butoxycarbonyl, tert-butoxycarbonyl, trichloroethoxycarbonyl, formyl, trifluoroacetyl or phenoxycarbonyl.

In the second such group, the 1,3,2',7', and 4" amino groups are protected with amino-protecting groups chosen from the same group listed for the first group of starting materials plus ethoxycarbonyl, the 1",3" and the 5,6 pairs of hydroxyl groups are each protected with an isopropylidene or cyclohexylidene group, and the group at the 6"-position is either hydroxyl, 2-methoxyprop-2-yl or 1-methoxycyclohex-1-yl. The group at C-6" can be 1-methoxycyclohex-1-yl only when the 2",3" and the 5,6 pairs of hydroxyl groups are each protected with a cyclohexylidene group. Analogously, the group at C-6" will be 2-methoxyprop-2-yl only when the pairs of hydroxy groups are each protected with an isopropylidene group. Finally, this invention does not relate to the compounds wherein the 2",3" and the 5,6 pairs of hydroxyl groups are each protected with a cyclohexylidene group, the group at the C-6" position is either hydroxy or 1-methoxycyclohex-1-yl and the 1,3,2',7' and 4" amino groups are protected with ethoxycarbonyl groups.

In describing this invention, the term "$C_1$ to $C_3$-alkylsulfonyloxy" means methanesulfonyloxy, ethanesulfonyloxy or n-propanesulfonyloxy with the preferred group being methanesulfonyloxy.

Similarly, the term "substituted phenylsulfonyloxy" indicates a phenylsulfonyloxy substituent mono-substituted at either the ortho, meta or para position of the phenyl ring with a substituent chosen from chloro, bromo, iodo, nitro, methyl or methoxy. Examples of such substituted phenylsulfonyloxy substituents include para-toluenesulfonyloxy, para-methoxyphenylsulfonyloxy, para-chlorophenylsulfonyloxy, para-bromophenylsulfonyloxy, para-iodophenylsulfonyloxy, para-nitrophenylsulfonyloxy, meta-methylphenylsulfonyloxy, meta-metoxyphenylsulfonyloxy, meta-bromophenylsulfonyloxy, meta-nitrophenylsulfonyloxy, ortho-chlorophenylsulfonyloxy, ortho-iodophenylsulfonyloxy and the like, with para-toluenesulfonyloxy being the preferred group.

In the description of the instant invention, the term "$C_1$ to $C_3$-alkylthio" indicates the methylthio, ethylthio and n-propylthio groups.

The term "$C_1$ to $C_4$-alkoxycarbonyl" means methoxycarbonyl, ethoxycarbonyl, n-propoxycarbonyl, iso-propoxycarbonyl, n-butoxycarbonyl and tert-butoxycarbonyl moieties.

As used in the instant application, the term "pharmaceutically acceptable acid addition salts" means those formed by standard acid-base reactions between the appropriate aminoglycoside and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, salicylic, methanesulfonic, benzenesulfonic, sorbic, picric, benzoic, cinnamic and like acids.

The method for preparing apramycin is described in U.S. Pat. Nos. 3,691,279 and 3,853,709, where apramycin is referred to as "nebramycin factor II." The subject matter in both U.S. Pat. Nos. 3,691,279 and 3,853,709 is herein incorporated by reference.

In order to better illustrate the synthetic relationship among the starting materials, intermediates and antibiotics claimed in the instant application, the following Scheme is supplied:

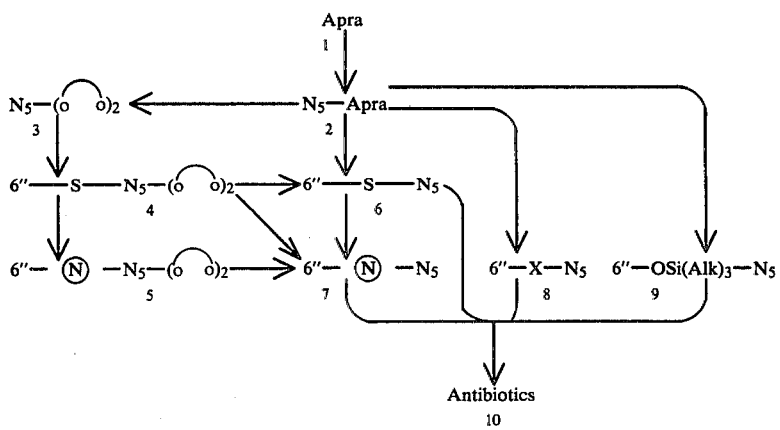

In the Scheme, "Apra" stands for apramycin. In the terms of the Scheme, if "Apra" is not explicitly listed, it is implied in the term. The symbol "N$_5$" indicates that the 1,3,2',7' and 4"-amino groups of apramycin are substituted by a suitable acyl protecting group. The symbol "(ö ö)$_2$" means that the 5,6 and 2",3" pairs of vicinal hydroxy groups are each protected with a cyclohexylidene or an isopropylidene protecting group.

The symbol "S" stands for a sulfonate group of the formula —OSO$_2$R, wherein R can be methyl, ethyl, n-propyl or a phenyl ring optionally substituted with either chloro, bromo, iodo, nitro, methyl or methoxy. The symbol "X" stands for chloro or bromo, and the symbol "—OSi(Alk)$_3$" stands for the tert-butyldimethylsilyloxy group.

Finally, in the Scheme, the symbol Ⓝ means azido, fluoro, bromo, iodo, methylthio, ethylthio, n-propylthio, phenylthio or cyano.

The starting materials shown in the Scheme which are provided in the instant application are 1,3,2',7',4"-penta-N-protected apramycin compounds ("penta-N-protected apramycin", 2), and 1,3,2',7',4"-penta-N-protected-5,6;2",3"-tetra-O-di(alkylidene)-apramycin compounds ("penta-N-protected-di(O-alkylidene)-apramycin", 3).

The penta-N-protected apramycin (2) has either formyl, trifluoroacetyl, trichloroethoxycarbonyl, methoxycarbonyl, propoxycarbonyl, iso-propoxycarbonyl, n-butoxycarbonyl, t-butoxycarbonyl, phenoxycarbonyl or benzyloxycarbonyl as the amino protecting group. These various amino-protected apramycin starting materials can be synthesized by methods well known to those skilled in the art, for example, by the various methods listed in T. W. Greene, *Protective Groups in Organic Synthesis*, J. Wiley and Sons, 1981, pp. 218–266. For example, when the N-protecting group is trichloroethoxycarbonyl, methoxycarbonyl, propoxycarbonyl, iso-propoxycarbonyl, n-butyoxycarbonyl, t-butoxycarbonyl, benzyloxycarbonyl or phenoxycarbonyl, the penta-N-protected apramycin derivatives can be synthesized by reacting apramycin with the appropriate number or slight excess of molar equivalents of an acylating agent, represented by the following general formula

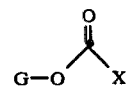

wherein G is methyl, propyl, iso-propyl, n-butyl, t-butyl, trichloroethyl, phenyl or benzyl and X is chloro, para-nitrophenoxy, N-oxysuccinimide, N-oxyphthalimide, and, when G is t-butyl, a group of the formula

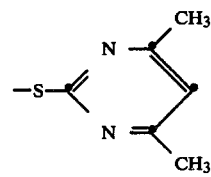

or a group of the formula

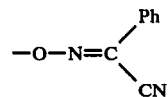

(the latter reagent is available from Aldrich Chemicals under the trademark BOC-ON ®).

The penta-N-formyl-apramycin starting material can be synthesized by reacting apramycin with the requisite number or slight excess of molar equivalents of an anhydride of formic acid. Similarly, the penta-N trifluoroacetylapramycin starting material is synthesized by reacting apramycin with trifluoroacetic anhydride or methyl trifluoroacetate.

The synthesis of the penta-N-protected di(O-alkylidene)apramycin intermediate (3) from the penta-N-protected apramycin (2) proceeds via initial formation of 1,3,2',7',4"-penta-N-protected-5,6;2",3"-tetra-O-di(alkylidene)-6"-O-(methoxyalkylidene)-apramycin ("6"-O-ketal compound", not shown in the Scheme) since the formation of the 6"-O-ketal compound occurs simultaneously with protection of the 2",3" and the 5,6 pairs of vicinal hydroxy groups. The 6"-ketal can be selectively hydrolyzed under mild acidic conditions to give the penta-N-protected-di(-O-alkylidene)apramycin (3). The alkylidene group in the intermediate penta-N-protected-di-(O-alkylidene)-apramycin is either the cyclohexylidene group or the isopropylidene group.

Methods for preparing such alkylidene derivatives are well known to those skilled in the art, as described generally in T. W. Greene, *Protective Groups in Organic Synthesis*, J. Wiley and Sons, New York, pp 72–86. A specific procedure for synthesizing the isopropylidene-protected starting material (3) is described in Example 4 wherein 1,3,2',7',4''-penta-N-benzyloxycarbonylapramycin is reacted with 2,2-dimethoxypropane and para-toluenesulfonic acid (as the acid catalyst) in a dimethylformamide/benzene solvent system followed by selective hydrolysis of the 6''-O-ketal in aqueous acetic acid. A specific procedure for isolating the 6''-O-ketal intermediate is given in Example 3, using essentially the same conditions as in Example 4, but omitting the hydrolysis of the 6''-O-ketal so that 6''-O-(2-methoxy-2-propyl)-2'',3'';5,6-tetra-O-diisopropylidenepenta-N-benzyloxycarbonylapramycin is obtained.

The next step in the synthesis of the apramycin antibiotics of this invention is the conversion of penta-N-protected apramycin (2) or penta-N-protected-di-(O-alkylidene)apramycin (3) to the corresponding 6''-O-sulfonate-1,3,2',7',4''-penta-N-protected apramycin (6''-O-sulfonate-penta-N-protected apramycin, 6) or 6''-O-sulfonate-1,3,2',7'4''-penta-N-protected-2'',3'';5,6-tetra-O-di(alkylidene)apramycin("6''-O-sulfonate-penta-N-protected-di(O-alkylidene)apramycin", 4), respectively. These conversions are carried out by treating either penta-N-protected apramycin (2) or penta-N-protected-di(O-alkylidene)apramycin (3) with the appropriate sulfonyl chloride in the presence of a base suitable for neutralizing the acid produced in the reaction. The preferred base is pyridine, which can also be used as the solvent for the reaction. The 6''-O-sulfonate-penta-N-protected apramycin intermediate (6) can also be obtained from the 6''-O-sulfonate-penta-N-protected-di-(O-alkylidene)apramycin (4) by acidic hydrolysis of the two alkylidene groups. The general conditions for acid-catalyzed hydrolysis applicable to this reaction are well known to those skilled in the art and are discussed in T. W. Greene, ibid., pp. 76–79.

The next step in the synthesis of apramycin antibiotics (10, formula A) involves the nucleophilic displacement of the 6''-O-sulfonate group of the 6''-O-sulfonate-penta-N-protected apramycin (6) or 6''-O-sulfonate-penta-N-protected-di(O-alkylidene)apramycin (4) to yield 6''-(nucleophile)-6''-deoxy-1,3,2',7',4''-penta-N-protected-apramycin ("6''-(nucleophile)-penta-N-protected apramycin", 7) and the 6''-(nucleophile)-6''-deoxy-1,3,2',7',4''-penta-N-protected-2'',3'';5,6-tetra-O-di(alkylidene)apramycin("6''-(nucleophile)-penta-N-protected-di(O-alkylidene)apramycin", 5), respectively. Nucleophiles represented by the term "nucleophile" are chosen from the group of azido, iodo, bromo, fluoro, methylthio, ethylthio, n-propylthio, phenylthio and cyano. Conditions for optimizing nucleophilic displacement reactions are found in an advanced organic chemistry textbook, such as T. H. Lowry and K. S. Richardson, *Mechanism and Theory in Organic Chemistry*, Harper and Row, New York, 1976, pages 84–90 and pages 170–209.

More specifically, the intermediates where the 6''-nucleophile is azido are synthesized by reacting either 6''-O-sulfonate-penta-N-protected apramycin (6) or 6''-O-sulfonate-penta-N-protected-di-(O-alkylidene)apramycin (4; (6) and (4) are referred to collectively as the "6''-O-sulfonate compounds") with an azide salt such as lithium azide in a polar, aprotic solvent such as dimethylformamide.

The intermediate compound where the 6''-nucleophile is iodo (5, 7) is obtained by reacting a 6''-O-sulfonate compound (4, 6) with sodium iodide in acetone. In an analogous manner, the intermediate compound where the 6''-nucleophile is bromo (5, 7) is prepared by reacting a 6''-O-sulfonate compound (4, 6) with lithium bromide in a polar aprotic solvent. Likewise, the 6''-nucleophile compound wherein the nucleophile is fluoro (5, 7) is synthesized by reacting a 6''-O-sulfonate compound (4, 6) with tetraethylammonium fluoride or tetrabutylammonium fluoride in a polar, aprotic solvent.

The 6''-nucleophile intermediate where the nucleophile is a thiol (5, 7) is synthesized by displacing the sulfonate group of a 6''-O-sulfonate compound (4, 6) with the appropriate thiol (methylthiol, ethylthiol, n-propylthiol or phenylthiol) in an aprotic solvent such as acetone or dimethylformamide.

Finally, the synthesis of the 6''-nucleophile intermediate compounds where the nucleophile is cyano (5, 7) entails reacting the 6''-O-sulfonate compounds (4, 6) with either (1) sodium or potassium cyanide in a polar, aprotic solvent or (2) potassium or sodium cyanide complexed with dicyclohexyl-18-crown-6 or 18-crown-6, respectively, in tetrahydrofuran.

The 6''-nucleophile-penta-N-protected-di(O-alkylidene) compounds (5) described above are converted to the corresponding 6''-nucleophile-penta-N-protected apramycin (7) before the N-protecting groups are removed to yield the antibiotic compounds (10) of this invention. The conversion parallels the conversion of the 6''-O-sulfonate-penta-N-protected-di(O-alkylidene)apramycin (4) to the corresponding 6''-O-sulfonate-penta-N-protected apramycin (6), that is, acid catalyzed hydrolysis of the two alkylidene groups.

As a final note, the reaction of 6''-O-sulfonate-penta-N-protected-di-(O-alkylidene)apramycin (4) with sodium iodide in dimethylformamide displaces the sulfonate group and removes the two alkylidene groups at the same time to yield the 6''-iodo-6''-deoxy-penta-N-protected apramycin (7).

An alternative synthesis of the 6''-(bromo or chloro)-6''-deoxy-penta-N-protected apramycin (8) involves reacting an anhydrous pyridine solution of penta-N-protected apramycin (2) with triphenylphosphine and N-bromosuccinimide or N-chlorosuccinimide, respectively.

The synthesis of 6''-O-(tert-butyldimethylsilyl)-penta-N-protected apramycin (9) involves reacting tert-butyldimethylsilyl chloride with either (a) an anhydrous dimethylformamide/benzene system containing the penta-N-protected apramycin (2) and imidazole or (b) an anhydrous pyridine solution of penta-N-protected apramycin (2).

The final step in the synthesis of the antibiotic compounds (10) of the instant invention is accomplished by the removal of the five amino-protecting groups. As shown in the Scheme, the immediate precursers to the antibiotic compounds are the 6''-O-sulfonate-penta-N-protected apramycins (6), 6''-(nucleophile)-penta-N-protected apramycins (7), the 6''-(bromo or chloro)-6''-deoxy-penta-N-protected apramycins (8) and the 6''-O-(tert-butyldimethylsilyl)penta-N-protected apramycin (9). The removal of the five amino protecting groups is effected by either acidic hydrolysis, basic hydrolysis or hydrogenation over a palladium catalyst. The conditions selected will depend on their compatibility with the purpose of either preserving or reducing the 6''-substituent. The deprotection step may be divided into two general classes, one class being deprotection without modification of the 6″-substituent and the other class being the deprotection of the amino groups with simultaneous reduction of the 6″ substituent.

The first class of deprotection reactions, i.e., deprotection of five amino groups without modification of the 6″-substituent, may utilize basic hydrolysis, such as removal of the phenoxycarbonyl or ethoxycarbonyl protecting groups with barium hydroxide in an aqueous alcohol, or acidic hydrolysis, such as removal of the tert-butoxycarbonyl groups with aqueous trifluoroacetic acid. It should be noted that the acidic conditions sufficient for the removal of the tert-butoxycarbonyl group would also result in the simultaneous removal of the two isopropylidene (or cyclohexylidene) vicinal hydroxy-protecting groups if they had not been previously hydrolysed. Hydrogenation of the five amino protecting groups in this first class of deprotection reactions, such as hydrogenation of benzyloxycarbonyl groups over a palladium catalyst, may be utilized if the 6″-substituent is not reduced by these conditions. Examples of compounds produced by such conditions include 6″-fluoro-6″-deoxyapramycin, 6″-chloro-6″-deoxyapramycin, 6″-O-(tert-butyldimethylsilyl)apramycin, 6″-O-(methanesulfonyl)apramycin and 6″-O-(toluenesulfonyl)apramycin (10).

The second general class of deprotection reactions involves not only removal of the five amino protecting groups but also the reduction of the 6″-substituent. This second class of deprotection reactions utilizes an amino-protecting group, such as benzyloxycarbonyl, that is removed by hydrogenation. This class of reaction yields 6″-deoxyapramycin, 6″-amino-6″-deoxyapramycin and 6″-(—CH$_2$—NH$_2$)—6″-deoxyapramycin antibiotic compounds (10).

The synthesis of 6″-deoxyapramycin (10) entails hydrogenation over a palladium catalyst of 6″-bromo, 6″-iodo or 6″-(alkyl or phenyl)thio-6″-deoxy-penta-N-benzyloxycarbonylapramycin intermediate compounds.

The synthesis of 6″-amino-6″-deoxyapramycin (10) entails hydrogenation of 6″-azido-6″-deoxy-penta-N-benzyloxycarbonylapramycin (7). The conditions used for this reaction parallel those for the synthesis of 6″-deoxyapramycin.

Finally, the synthesis of 6″-(CH$_2$—NH$_2$)-6″-deoxyapramycin (10) involves hydrogenation of 6″-cyano-6″-deoxy-penta-N-benzyloxycarbonylapramycin (7). The conditions used for this reaction parallel those for the synthesis of 6″-deoxyapramycin.

The synthesis of the 6″-bromo, 6″-iodo and 6″-(alkyl or phenyl)thio-6″-deoxyapramycin antibiotics is accomplished by the reaction of the appropriate nucleophile with a 6″-(alkyl, phenyl or substituted phenyl)sulfonate apramycin antibiotic compound. For example, 6″-bromo-6″-deoxyapramycin is synthesized by reacting 6″-O-(p-toluenesulfonyl)apramycin with a bromide salt such as lithium bromide. Similarly, 6″-iodo-6″-deoxyapramycin is synthesized by reacting 6″-O-(methanesulfonyl)apramycin with an iodide salt such as sodium iodide. The synthesis of 6″-(thio substituted)-6″-deoxyapramycin, where the 6″-thio substituent is thiomethyl, thioethyl, thio(n-propyl) or thiophenyl can be synthesized by reacting one of the 6″-(alkyl, phenyl or substituted phenyl)sulfonate or 6″-bromo-6″-deoxy or 6″-iodo-6″-deoxyapramycin antibiotics (10) with either methylthiol, ethylthiol, n-propylthiol or phenylthiol.

Isolation and purification of the products in the above procedure can be accomplished by methods well known in the art, as exemplified by such procedures described in the Experimental Section.

The 6″-substituted-apramycin antibiotic compounds of this invention, either in their free base form or their pharmaceutically acceptable acid addition salt form, are useful for treating infections caused by gram-positive and gram-negative bacteria in warm-blooded animals. These compounds can be administered parenterally, in the free base form or in the pharmaceutically acceptable acid addition salt form, using pharmaceutically acceptable formulations known in the art. These compounds can also be administered as veterinary compositions, such as, for example, in the feed or drinking water of farm animals to treat infections such as colibacillosis or swine dysentery.

Alternatively, these compounds can be used as a surface disinfectant. Solutions containing as little as 0.1 percent by weight of the antibiotic are effective for disinfecting purposes. Such solutions, preferably also containing a detergent or other cleansing agent, are useful for disinfecting objects such as glassware, dental and surgical instruments, and surfaces such as walls, floors, and tables in areas where maintenance of sterile conditions is important, i.e. hospitals, food-preparation areas, and the like.

The antibacterial activity of the antibiotic compounds of this invention is illustrated by the following in vitro and in vivo test data obtained with representative compounds. In Tables I and II the minimum inhibitory concentration (MIC) for representative compounds against a wide range of gram-positive and gram-negative bacteria is presented. The MIC values were obtained by the standard agar dilution test.

TABLE 1

Antibiotic Activity of 6″-Substituted Derivatives of Apramycin vs. Gram-Negative Bacteria

| Test Organism* | Test Compound[1] Minimum Inhibitory Concentration (mcg/ml) | | | | | |
|---|---|---|---|---|---|---|
|  | 1 | 2 | 3 | 4 | 5 | 6 |
| Pseudomonas aeruginosa X48 | 128 | >128 | 16 | 4 | 32 | >128 |
| Pseudomonas aeruginosa X528 | 128 | >128 | 32 | 16 | 64 | 64 |
| Pseudomonas aeruginosa X239 | 128 | >128 | 8 | 4 | 32 | 128 |
| Pseudomonas aeruginosa Ps9 | >128 | >128 | 32 | 16 | 128 | >128 |
| Pseudomonas aeruginosa Ps15 | 128 | >128 | 16 | 4 | 32 | 128 |
| Pseudomonas aeruginosa Ps25 | 64 | >128 | 16 | 4 | 32 | 128 |
| Pseudomonas aeruginosa 4276 | >128 | >128 | 16 | 8 | 64 | 128 |
| Pseudomonas aeruginosa PI23 | >128 | >128 | >128 | >128 | >128 | >128 |
| Pseudomonas aeruginosa SF-2 | 128 | >128 | 16 | 8 | 32 | 128 |
| Serratia marcescens SE2 | 8 | 16 | 4 | 4 | 8 | 64 |

TABLE 1-continued

Antibiotic Activity of 6″-Substituted Derivatives of Apramycin
vs.
Gram-Negative Bacteria

| Test Organism* | Test Compound[1] Minimum Inhibitory Concentration (mcg/ml) | | | | | |
|---|---|---|---|---|---|---|
| | 1 | 2 | 3 | 4 | 5 | 6 |
| *Serratia marcescens* X99 | 4 | 16 | 4 | 2 | 8 | 32 |
| *Serratia marcescens* SE3 | 8 | 16 | 4 | 4 | 8 | 64 |
| *Enterobacter aerogenes* EB6 | 4 | 16 | 4 | 4 | 16 | 32 |
| *Enterobacter cloacae* EN453 | 8 | 16 | 4 | 4 | 8 | 32 |
| *Enterobacter cloacae* EB24 | 4 | 16 | 4 | 4 | 8 | 16 |
| *Proteus morganii* PR1 | 8 | 16 | 4 | 4 | 16 | 32 |
| *Proteus morganii* PR2 | 32 | 16 | 32 | 8 | 8 | 64 |
| *Proteus inconstans* PV25 | 8 | 16 | 4 | 2 | 8 | 16 |
| *Klebsiella pneumoniae* KL2 | 8 | 16 | 4 | 4 | 8 | 32 |

*Numerals and letters following the names of test microorganisms refer to the strains.
[1]Test compounds numbered 1-6 are as follows:
1 = 6″-O—(methanesulfonyl)apramycin
2 = 6″-O—(p-toluenesulfonyl)apramycin
3 = 6″-chloro-6″-deoxyapramycin
4 = 6″-deoxyapramycin
5 = 6″-amino-6″-deoxyapramycin
6 = 6″-O—(tert-butyldimethylsilyl)apramycin

TABLE II

Antibiotic Activity of 6″-Substituted Derivatives of Apramycin
vs.
Gram-Positive and Gram-Negative Bacteria

| Test Organism* | Test Compound[1] Minimum Inhibitory Concentration (mcg/ml) | | | | |
|---|---|---|---|---|---|
| | 1 | 2 | 3 | 4 | 5 |
| *Pseudomonas aeruginosa* X239 | 4 | 16 | 2 | 2 | NT |
| *Serratia marcescens* SE3 | 16 | 32 | 16 | 16 | 16 |
| *Enterobacter aerogenes* EB17 | 4 | NT | 16 | 4 | 8 |
| *Proteus morganii* PR15 | 32 | 16 | 8 | 8 | 32 |
| *Klebsiella pneumoniae* KL14 | 4 | 2 | 2 | 4 | 8 |
| *Staphylococcus aureus* 3055 | 2 | <0.5 | 1 | 2 | 1 |
| *Staphylococcus aureus* 3074 | 4 | 2 | 1 | 1 | 4 |
| *Streptococcus faecalis* X66 | 32 | 16 | 8 | 8 | 32 |
| *Salmonella typhosa* SA12 | 4 | 1 | 2 | 4 | 16 |
| *Escherichia coli* EC14 | 8 | 4 | 16 | 16 | 16 |
| *Citrobacter freundii* CF17 | 4 | 4 | 4 | 8 | 8 |
| *Bordetella bronchiseptica* 16 | 16 | 64 | 8 | 16 | 32 |
| *Salmonella typhimurium* | 4 | 4 | 8 | 16 | 8 |
| *Pseudomonas solanacearum* X185 | 1 | 1 | 2 | 4 | 4 |
| *Erwinia amylovora* | NT | 2 | 1 | 2 | 4 |

*Numerals and letters following the names of test microorganisms refer to the strains.
[1]Test compounds numbered 1-5 are as follows:
1 = 6″-O—(methanesulfonyl)apramycin
2 = 6″-O—(p-toluenesulfonyl)apramycin
3 = 6″-chloro-6″-deoxyapramycin
4 = 6″-deoxyapramycin
5 = 6″-amino-6″-deoxyapramycin Table III illustrates the effective dose ($ED_{50}$, effective dose to protect 50 percent of the test animals) for representative compounds of this invention against an experimental bacterial infection in mice.

TABLE III

Subcutaneous Therapy of *Pseudomonas aeruginosa* X239
Infections in Mice

| Test Compound | Effective Dose ($ED_{50}$)* |
|---|---|
| 6″-Deoxyapramycin | 10.9 |
| 6″-Amino-6″-deoxyapramycin | 15.0 |

*mg/kg × 2 subcutaneous doses at 1 and 5 hours post infections

The $ED_{50}$ values were determined as described by W. E. Wick et al., Journal of Bacteriolocy, 81 [No. 2], 233–235 (1961).

The following Examples (1 through 14) in the Experimental Section are provided to further illustrate this invention. It is not intended that this invention be limited in scope by reason of any of the following Examples.

In the following Experimental Section, carbon-13 nuclear magnetic resonance spectra, field desorption mass spectra, high performance liquid chromatography, thin layer chromatography and ultraviolet spectra are abbreviated C-13 n.m.r., f.d.m.s., HPLC, t.l.c., and u.v., respectively. The nuclear magnetic resonance spectra were obtained either on a Varian Associates FT-80 Spectrometer or a Jeol JNM-PS-100 Spectrometer using dioxane as the internal standard. The chemical shifts are expressed in δ values (parts per million downfield from tetramethylsilane). The term "pyridine-$d_5$" and the symbol "DMSO-$d_6$" stand for perdeuteriopyridine and perdeuteriodimethylsulfoxide, respectively. The field desorption mass spectra were taken on a Varian-MAT 731 Spectrometer using carbon dendrite emitters. The high performance liquid chromatography was carried out on a Waters Associates, Inc. Prep. 500 Instrument. Ultraviolet spectra were obtained using a Cary 118 Spectrometer.

Column chromatography is often carried out using an ion exchange resin such as Bio-Rex 70 as the stationary phase. Bio-Rex 70 is a weakly acidic cation exchange resin containing carboxylic acid groups on a macroreticular acrylic polymer lattice and is a product of Bio-Rad Labs, 2200 Wright Ave., Richmond, California 94804. Thin layer chromatography was carried out on E. Merck silica gel plates.

The abbreviations "mmol" and "h" stand for millimole and hour, respectively.

In the following Experimental Section the abbreviations "CBZ" and "CBE" stand for benzyloxycarbonyl and ethoxycarbonyl, respectively.

EXPERIMENTAL SECTION

Preparation 1

1,3,2′,7′,4″-Penta-N-CBE-Apramycin

Apramycin (13.5 g, 25 mmol) was dissolved in water (120 ml) and this solution was treated with sodium carbonate (10 g) followed by dilution with acetone (120 ml). This mixture was then stirred vigorously with a mechanical stirrer while ethyl chloroformate (14.7 g, 135 mmol) was added. The addition of the ethyl chloroformate produced as exothermic reaction and a precipitate. This reaction mixture was stirred for an additional 30 minutes past completion of the addition of ethyl chloroformate and was then allowed to stand overnight at room temperature. The precipitate was removed by filtration and was washed with 50% aqueous acetone. The filtrate was then concentrated to one-third of its original volume under reduced pressure, causing a gummy solid to precipitate. After the mother liquor was decanted, the gum was dissolved in methanol (35 ml) and this solution was filtered. The filtrate was evaporated to dryness to give 18.4 g of the desired 1,3,2',7',4''-penta-N-CBE-apramycin; C-13 n.m.r. (DMSO-d$_6$) $\delta$ 14.5, 29.7, 32.0, 34.6, 49.9 ($\times$2), 51.1, 53.3, 57.7, 59.3–59.6, 60.6, 60.9, 66.1, 69.5, 70.1, 71.9, 72.8, 73.9, 76.9, 82.1, 93.2, 95.0, 97.6, 155.4–156.6; f.d.m.s. m/e 900 (P+1).

EXAMPLE 1

1,3,2',7',4''-Penta-N-Formylapramycin

Apramycin (10.5 g) was dissolved in 98% formic acid (294 ml) and acetic anhydride (98 ml) was added dropwise over a 0.5 h period. The resultant solution was stirred at room temperature for 20 h and the solvent was then evaporated under reduced pressure. The resultant residue was taken up in toluene (200 ml) and this solution was evaporated to dryness.

The residue was dissolved in methanol (350 ml) and the pH of this solution was adjusted to 9.0 by the addition of solid sodium methoxide. The resultant solution was stirred overnight at room temperature, and the solvent was evaporated to give 9.3 g of the desired product, 1,3,2',7',4''-penta-N-formylapramycin.

EXAMPLE 2

1,3,2',7',4''-Penta-N-CBZ-Apramycin

Apramycin (27 g, 50 mmol) was dissolved in water (250 ml) and the solution was diluted with acetone (250 ml), treated with sodium carbonate (26.5 g, 250 mmol) and cooled in an ice bath. Benzyloxycarbonyl chloride (51.3 g, 300 mmol) was added dropwise with vigorous mechanical stirring. After stirring for 1 hour in an ice bath and 2.5 h at room temperature, the reaction mixture was extracted with ethyl acetate. The organic extracts were combined and were washed with saturated sodium chloride solution, dried over magnesium sulfate and filtered and the filtrate was evaporated under reduced pressure. The residue was dried at 40° C. in vacuo to give 61.0 g (100%) of 1,3,2',7',4''-penta-N-CBZ-apramycin.

C-13 n.m.r. (pyridine-d$_5$) $\delta$ 31.0, 33.1, 36.0, 51.6 ($\times$2), 52.8, 55.3, 59.3, 63.0, 66.4–67.0, 70.9, 71.9, 74.0, 74.8, 76.7, 78.4, 84.6, 95.7, 98.2, 100.4, 127.1–129.7, 137.5–138.7, 156.7–158.3; f.d.m.s. m/e=1210 (P+1).

EXAMPLE 3

6''-O-(2-Methoxy-2-Propyl)-2'',3''; 5,6-Tetra-O-Diisopropylidene-Penta-N-CBZ-Apramycin 1,3,2',7',4''-Penta-N-CBZ-apramycin (25 g) was dissolved in dimethylformamide (50 ml) and benzene (400 ml). This solution was treated with p-toluenesulfonic acid monohydrate (750 mg) and 2,2-dimethoxypropane (50 ml). The solvent was slowly distilled from this reaction mixture (100 ml/h) while simultaneously adding a solution composed of 2,2-dimethoxypropane (25 ml) in benzene (200 ml) during that period. After 4 h, the reaction mixture was cooled and diluted with ethyl acetate (250 ml) and the resultant solution was extracted twice with saturated sodium bicarbonate solution (200 ml, 100 ml). The organic layer from this extraction was separated, dried over sodium sulfate-potassium carbonate and filtered. The filtrate was evaporated to dryness under reduced pressure. The residue was then dissolved in dichloromethane (50 ml) and this solution was divided into two portions, each of which was loaded on a silica gel column (Waters Prep 500) packed in dichloromethane. Each of the two silica gel columns was eluted with a linear gradient of 1% ethanol in dichloromethane (4 l) and 4% ethanol in dichloromethane (4 l). Fractions containing the desired product were located by thin layer chromatography analysis and the appropriate fractions were combined and evaporated to dryness to yield 14.5 g of the desired product, 6''-O-(2-methoxy-2-propyl)-2'',3''; 5,6-tetra-O-diisopropylidene-1,3,2',7',4''-penta-N-CBZ-apramycin: C-13 n.m.r. (pryidine-d$_5$) $\delta$ 24.4, 24.5, 26.4–27.0, 30.6, 32.7, 37.0, 48.3, 50.0, 50.4, 51.7, 54.3, 59.8, 61.2, 66.3–67.4, 71.0, 74.3, 74.9, 77.0, 78.3, 79.3, 81.7, 94.4, 95.3, 96.8, 100.1, 110.6, 111.5, 128.0–128.8, 137.6–139.0, 156.5–157.3.

EXAMPLE 4

1,3,2',7',4''-Penta-N-CBZ-2'',3'',5,6-Tetra-O-Diisopropylidene-Apramycin 1,3,2',7',4''-Penta-N-CBZ-apramycin (50 g, 41.3 mmol) was dissolved in benzene (800 ml) and dimethylformamide (120 ml) and then treated with 2,2-dimethoxypropane (100 ml) and p-toluenesulfonic acid monohydrate (1.5 g). The solution was refluxed with slow removal of the volatiles (300 ml/7 h); a solution of dimethoxypropane (12 ml) in benzene (100 ml) was added after 2 h and after 4 h in order to replenish the reagent and the solvent.

After 7 h, the solution was cooled, diluted with ethyl acetate (400 ml) and extracted with saturated sodium bicarbonate solution (200 ml). The organic solution was separated, dried over sodium sulfate-potassium carbonate and filtered and the filtrate was evaporated under reduced pressure. The resultant residue (60 g) was dissolved in methanol (800 ml) and the solution was diluted with water (150 ml) and treated with glacial acetic acid (10 ml). After 6 h at room temperature, this reaction mixture was made basic with 5 N sodium hydroxide and concentrated to aqueous under reduced pressure, yielding a precipitate. Chloroform (500 ml) was added to dissolve the precipitate and the organic layer was separated, extracted with saturated sodium bicarbonate solution (150 ml), dried over sodium sulfate-potassium carbonate and filtered. The filtrate was evaporated under reduced pressure and the resultant crude product (54 g) was divided into three portions, each of which was chromatographed on silica gel using a Waters Prep 500 instrument; samples were loaded on the column in dichloromethane solution and eluted with a linear gradient of 2% ethanol in dichloromethane (4 l) and 6% ethanol in dichloromethane (4 l). Fractions containing the desired product were located by thin layer chromatography analysis, and these fractions were combined and were evaporated under reduced pressure to yield 26.4 g (50%) of 1,3,2',7',4''-penta-N-CBZ-2'',3''; 5,6-tetra-O-diisopropylidene-apramycin: C-13 n.m.r. (pyridine-d$_5$) $\delta$ 26.5–27.0, 30.7, 33.0, 37.0, 49.8, 50.4, 51.7, 54.0, 59.0, 62.2, 66.3–67.0, 71.0, 74.3, 76.6, 77.2, 78.2, 79.4, 81.8, 93.8, 94.6, 96.7, 110.7, 111.5, 127.8–128.8, 137.4–139.1, 156.5–157.4.

EXAMPLE 5

6''-O-(Para-toluenesulfonyl)apramycin

Step A: Preparation of 6''-O-(p-toluenesulfonyl)-1,3,2',7',4''-penta-N-CBZ-apramycin 1,3,2',7',4''-Penta-N-CBZ-apramycin (5.0 g, 4.13 mmol) was dissolved in pyridine (120 ml) and 40 ml of pyridine was distilled. The remaining anhydrous solution was cooled in an ice bath, treated with a solution of p-toluenesulfonyl chloride (863 mg, 4.54 mmol) in pyridine (8 ml) and stirred for 1.5 h at 0° C. and then overnight at room temperature. The mixture was evaporated to dryness and the residue was dissolved in dichloromethane (150 ml) and sequentially extracted with 1 N hydrochloric acid (2×20 ml), 5% sodium bicarbonate solution (2×20 ml) and saturated sodium chloride solution (20 ml). The dichloromethane layer was dried over sodium sulfate and filtered and the filtrate was evaporated to dryness. The residue was dissolved in dichloromethane and chromatographed on silica gel (Waters Prep 500 Instrument), eluting with a linear gradient of 3% ethanol in dichloromethane (4 l) and 8% ethanol in dichloromethane (4 l). Fractions containing the desired product were located by thin layer chromatography analysis, combined and evaporated to dryness to give 1.45 g of 6''-O-(p-toluenesulfonyl)-1,3,2',7',4''-penta-N-CBZ-apramycin.

Step B: Preparation of the 6''-O-(p-toluenesulfonyl)apramycin

6''-O-(p-toluenesulfonyl)-1,3,2',7',4''-penta-N-CBZ-apramycin (1.0 g, 0.74 mmol) from Step A was dissolved in ethanol (50 ml) and the solution was diluted with water (20 ml) and was hydrogenated (1 atm $H_2$) over 5% palladium/carbon (1.0 g) overnight at room temperature. The catalyst was removed by filtration and the filtrate was evaporated. The resultant residue was dissolved in water (6 ml) and loaded onto a column of BioRex 70 (100 ml, $NH_4^+$ cycle, pH 9.2). The column was eluted with 0.01 N ammonium hydroxide solution followed by a linear gradient of 0.01 N ammonium hydroxide (600 ml) and 0.1 N ammonium hydroxide (600 ml). Fractions containing the desired product were located by thin layer chromatography analysis, combined and lyophilized to yield 90 mg. of 6''-O-(p-toluenesulfonyl)apramycin.

C-13 n.m.r. ($H_2O$—$D_2O$, pH 9–11) δ 21.9, 33.0 (×2), 36.8, 49.9, 50.4, 51.3, 53.0, 62.2, 66.2, 67.9, 71.0, 71.6, 71.8, 73.4, 74.1, 76.9, 78.5, 88.0, 95.4, 96.4, 101.5, 126.2, 128.8, 130.3, 131.0; u.v. ($H_2O$) $\lambda_{max}$=224 nm (ε=10,000).

EXAMPLE 6

6''-O-(p-Toluenesulfonyl)-1,3,2',7',4''-Penta-N-CBE-Apramycin 1,3,2',7',4''-Penta-N-CBE-apramycin (450 mg, 0.5 mmol) was dissolved in pyridine (8 ml) and this solution was cooled in an ice bath and then treated with a solution of p-toluenesulfonyl chloride (310 mg, 1.62 mmol) in pyridine (2 ml). The reaction mixture was stirred for 1 hour at 0° C. and overnight at room temperature. The solvent was then evaporated from this reaction mixture under reduced pressure and the resultant residue was dissolved in chloroform (60 ml) and was extracted with 5% sodium bicarbonate solution (10 ml) and then water (10 ml). The organic layer was separated, dried over sodium sulfate and filtered and the filtrate was evaporated to dryness. The residue was dissolved in chloroform and loaded onto a column of silica gel (50 g, Grace 62) packed in chloroform. The column was eluted stepwise with solutions of ethanol in chloroform, each solution containing an increasing amount of ethanol (3%, 5%, 8% and 10%). Fractions containing the desired product were located by thin layer chromatography analysis and the appropriate fractions were combined and evaporated to dryness to yield 225 mg of the desired product, 6''-O-toluenesulfonyl-1,3,2',7',4''-penta-N-CBE-apramycin; C-13 n.m.r. (DMSO-$d_6$) δ 14.5, 21.0, 29.8, 31.8, 34.7, 50.0 (×2), 51.1, 53.1, 57.6, 59.4–59.7, 60.7, 66.2, 69.6, 70.0 (×2), 71.4, 74.0, 76.9, 82.3, 93.6, 95.4, 97.7, 127.6, 129.9, 132.0, 133.4, 144.8, 155.5–157.2.

EXAMPLE 7

6''-O-(Methanesulfonyl)apramycin

Step A: Preparation of 2'',3'';5,6-Tetra-O-Diisopropylidene-1,3,2',7',4''-penta-N-CBZ-6''-O-(methanesulfonyl)apramycin 2'',3'';5,6-Tetra-O-Diisopropylidene-penta-N-CBZ-apramycin (645 mg, 0.5 mmol) was dissolved in pyridine (5 ml), cooled in an ice bath and treated with methanesulfonyl chloride (200 mg, 1.65 mmol) dissolved in pyridine (5 ml). After the resultant mixture was stirred for 3 h at 0° C., the mixture was filtered and evaporated to dryness to yield 2'',3'';5,6-Tetra-O-diisopropylidene-1,3,2',7',4''-penta-N-CBZ-6''-O-(methanesulfonyl)apramycin.

Step B: Preparation of Penta-N-CBZ-6''-O-(methanesulfonyl)apramycin

The diisopropylidene-CBZ-6''-O-(methanesulfonyl)apramycin from Step A was dissolved in cold trifluoroacetic acid (5 ml)-water (0.5 ml) at 0° C. and stirred for 1 h. Volatile material was removed under reduced pressure and the residue was treated with 5% sodium bicarbonate solution (10 ml) and extracted with chloroform (80 ml). The chloroform layer was separated and extracted sequentially with 5% sodium bicarbonate solution (15 ml), 1 N hydrochloric acid (10 ml), 5% sodium bicarbonate solution (10 ml) and water; the chloroform layer was then dried over sodium sulfate and filtered and the filtrate was evaporated to dryness.

Step C: Preparation of 6''-O-(Methanesulfonyl)apramycin

The resultant residue was dissolved in ethanol (17 ml) and diluted with water (8 ml) and then hydrogenated (1 atm $H_2$) over 5% palladium/carbon (640 mg) overnight at room temperature. The catalyst was removed by filtration and the filtrate was evaporated to dryness. The residue was dissolved in 0.01 N ammonium hydroxide (5 ml) and loaded on a column of BioRex 70 (30 ml, $NH_4^+$ cycle, pH 10.0). The column was eluted stepwise with dilute ammonium hydroxide solutions (0.01 N to 0.07 N). Fractions containing the desired product were located by thin layer chromatography analysis, and these fractions were combined and were lyophilized to yield 179 mg of 6''-O-(methanesulfonyl)apramycin:

C-13 n.m.r. ($H_2O$-$D_2O$, pH 9–11) δ 32.8, 33.0, 36.5, 37.6, 49.9, 50.4, 51.3, 53.0, 62.2, 66.2, 68.0, 70.3, 71.0, 71.6, 72.0, 73.4, 76.9, 78.4, 87.7, 95.3, 96.6, 101.5; f.d.m.s. m/e=618 (P+1).

EXAMPLE 8

6"-Iodo-6"-Deoxy-1,3,2',7',4"-Penta-N-CBZ-Apramycin

Step A: Preparation of 6"-O-(methanesulfonyl)-2",3";5,6-Tetra-O-diisopropylidene-1,3,2',7',4"-penta-N-CBZ-apramycin.

2",3";5,6-Tetra-O-diisopropylidene-1,3,2',7',4"-penta-N-CBZ-apramycin (970 mg, 0.75 mmol) was dissolved in pyridine (20 ml) and cooled to 0° C. The solution was treated dropwise with a solution composed of methanesulfonyl chloride (300 mg, 2.6 mmol) in pyridine (5 ml) and this reaction mixture was stirred at 0° C. for 3 h; at the end of this time, the precipitate that had formed was removed by filtering the reaction mixture through a pad of Celite and the filtrate was evaporated to dryness under reduced pressure. The resultant residue was dissolved in chloroform (90 ml) and extracted sequentially with 1 N hydrochloric acid (15 ml), 5% sodium bicarbonate solution (10 ml) and water (10 ml). The organic layer was separated, dried over sodium sulfate and filtered and the filtrate was evaporated under reduced pressure.

Step B: Preparation of 6"-iodo6"-deoxy-2",3";5,6-diisopropylidene-penta-N-CBZ-apramycin.

The 6"-O-(methanesulfonyl)-diisopropylidenepenta-N-CBZ-apramycin compound prepared above was dissolved in acetone (45 ml), and this solution was treated with a solution composed of sodium iodide (1.69 g, 11.3 mmol) in acetone (25 ml). The resultant reaction mixture was heated at 92° C. for 17 h. The reaction mixture was then cooled and filtered and the filtrate was evaporated to dryness. The resultant residue was dissolved in chloroform (100 ml) and extracted with water and then 5% sodium thiosulfate solution. The organic layer was separated, dried over sodium sulfate and filtered and the filtrate was evaporated under reduced pressure to give the desired intermediate, 6"-iodo-6"-deoxy-2",3";5,6-tetra-O-diisopropylidene-1,3,2',7',4"-penta-N-CBZ-apramycin.

Step C: Preparation of 6"-iodo-6"-deoxy-1,3,2',7',4"-penta-N-CBZ-apramycin.

The 6"-iodo-6"-deoxy-diisopropylidenepenta-N-CBZ-apramycin prepared above was dissolved in a solution composed of cold trifluoroacetic acid (8 ml) and water (0.9 ml). This solution was stirred at 0° C. for 40 minutes and was then concentrated under reduced pressure, diluted with toluene and evaporated to dryness. The resultant residue was dissolved in chloroform (100 ml) and this solution was extracted with 5% sodium bicarbonate solution (10 ml) and then water (10 ml). The organic extract was then separated, dried over sodium sulfate and filtered, and the filtrate was evaporated under reduced pressure to yield 700 mg of the desired product, 6"-iodo-6"-deoxy-1,3,2',7',4"-penta-N-CBZ-apramycin.

EXAMPLE 9

6"-Iodo-6"-Deoxy-1,3,2',7',4"-Penta-N-CBZ-Apramycin

A solution composed of Penta-N-CBZ-6"-O-(methanesulfonyl)apramycin (26 mg, 0.02 mmol) in dimethylformamide (2 ml) was treated with a solution of sodium iodide (30 mg, 0.2 mmol) in dimethylformamide (2 ml). This solution was heated at 100° C. for 5 h and was then cooled and the solvent was evaporated under reduced pressure. The resultant residue was partitioned between chloroform and water, and the organic layer was separated, dried over sodium sulfate and filtered. The filtrate was evaporated to dryness to yield the desired product, 6"-iodo-6"-deoxy-1,3,2',7',4"-penta-N-CBZ-apramycin.

EXAMPLE 10

6"-Bromo-6"-Deoxy-Penta-N-CBZ-Apramycin

Penta-N-CBZ-apramycin (605 mg, 0.5 mmol) was dissolved in pyridine (27 ml) and a portion (17 ml) of the solvent was distilled in order to render the remaining solution anhydrous. This anhydrous solution was cooled in an ice bath and treated with triphenylphosphine (331 mg, 1.25 mmol) and N-bromosuccinimide (222 mg, 1.25 mmol). The resultant brown mixture was stirred overnight at room temperature and then quenched with methanol (1.5 ml) and evaporated to dryness. The resultant residue was dissolved in dichloromethane (70 ml) and extracted sequentially with 1 N hydrochloric acid (2×15 ml), 5% sodium bicarbonate solution (10 ml) and saturated sodium chloride solution. The organic layer was separated, dried over sodium sulfate, filtered and evaporated to dryness. The resultant residue was triturated with ether (2×50 ml) and the insoluble product was filtered, washed with ether and air dried to yield 485 mg (76%) of 6"-bromo-6"-deoxy-penta-N-CBZ-apramycin.

C-13 n.m.r. (pyridine-$d_5$) δ 31.1, 33.3, 35.1, 35.9, 51.6 (×2), 52.8, 57.8, 59.3, 66.2–67.3, 70.8, 71.7, 72.7, 73.6, 76.6, 78.0, 84.5, 95.7, 97.8, 100.2, 127.8–128.7, 137.6–138.7, 156.6–158.3; f.d.m.s. m/e=1272 and 1274 (P+1).

EXAMPLE 11

6"-Deoxyapramycin

Method 1

6"-Bromo-6"-deoxy-penta-N-CBZ-apramycin (2.0 g, 1.6 mmol) was dissolved in 2:1 ethanol:water (100 ml) containing triethylamine (0.22 ml) and then hydrogenated at 1 atm $H_2$ pressure over 5% palladium/carbon (2 g) at room temperature overnight. The catalyst was removed by filtration and the filtrate was concentrated to aqueous, filtered again and lyophilized. The residue was dissolved in 0.01 N ammonium hydroxide (15 ml) and loaded on a column of BioRex 70 (100 ml, $NH_4^+$ cycle, pH 10). The column was eluted with a linear gradient of 0.01 N ammonium hydroxide (600 ml) and 0.1 N ammonium hydroxide (600 ml). Fractions containing the desired product were located by thin layer chromatography analysis, combined and lyophilized to yield 445 mg of 6"-deoxyapramycin. C-13 n.m.r. ($H_2O$-$D_2O$, pH 9-11) δ 17.9, 32.9 (×2), 35.7, 49.7, 50.2, 51.2, 53.6, 62.3, 66.2, 67.9, 70.4, 71.0, 71.9, 73.2, 76.7, 77.5, 87.2, 95.2, 96.3, 101.1, f.d.m.s. m/e=524 (P+1).

Method 2

Step A: Preparation of 2",3";5,6-Diisopropylidene-penta-N-CBZ-6"-O-(methanesulfonyl)apramycin.

2",3";5,6-Diisopropylidene-penta-N-CBZ-apramycin (1.44 g, 1.11 mmol) in pyridine (30 ml) was treated at 0° C. with methanesulfonyl chloride (444 mg, 3.9 mmol) in cold pyridine (10 ml) as in Example 8 to yield the 6"-O-methanesulfonyl intermediate.

Step B: Preparation of 6″-Iodo-6″-deoxypenta-N-CBZ-apramycin.

The diisopropylidene-penta-N-CBZ-methanesulfonyl derivative from Step A was dissolved in dimethylformamide (20 ml) and added to a solution of sodium iodide (1.67 g, 11.1 mmol) in dimethylformamide (20 ml) to which had been previously added 0.15 ml of a solution of triethylamine (1.0 ml) in dimethylformamide (9 ml). The resultant mixture was heated at 100° C. with stirring for 3 h. The solution was cooled and filtered and the filtrate was evaporated to dryness. The residue was dissolved in dichloromethane (80 ml) and sequentially extracted with 5% sodium bicarbonate solution (10 ml), water (10 ml), 5% sodium thiosulfate solution (15 ml) and water. The dichloromethane solution was separated, dried over sodium sulfate and filtered and the filtrate was evaporated to dryness.

Step C: Preparation of 6″-Deoxyapramycin.

The 6″-iodo-6″-deoxyapramycin derivative synthesized in Step B was dissolved in ethanol (17 ml) and the solution was diluted with water (5 ml) and triethylamine (0.22 ml) and hydrogenated (1 atm $H_2$) over 5% palladium/carbon (1.43 g) overnight at room temperature. The catalyst was filtered and the filtrate was evaporated to dryness. The residue was dissolved in water (3 ml) and loaded on a column of BioRex 70 ($NH_4^+$ cycle). The column was eluted stepwise with 100 ml volumes of dilute ammonium hydroxide solution (0.01 N to 0.08 N). Fractions containing the desired product were located by thin layer chromatography analysis, combined and lyophilized to yield 403 mg of 6″-deoxyapramycin.

EXAMPLE 12

6″-O-(tert-Butyldimethylsilyl)Apramycin

Method 1

Step A: Preparation of 6″-O-(tert-butyldimethylsilyl)-penta-N-CBZ-apramycin.

Penta-N-CBZ-apramycin (5.0 g, 4.13 mmol) was dissolved in dimethylformamide (50 ml)-benzene (50 ml), and then 38 ml of solvent from the resultant solution was distilled. The resultant anhydrous solution was cooled to room temperature and treated with imidazole (760 mg, 11.2 mmol) and tert-butyldimethylsilyl chloride (805 mg, 5.36 mmol). The resultant solution was stirred at 35° C. for 6 h and then evaporated under reduced pressure. The residue was dissolved in dichloromethane (60 ml) and this solution was extracted sequentially with 1 N hydrochloric acid, 5% sodium bicarbonate solution and saturated sodium chloride solution. The dichloromethane layer was dried over sodium sulfate and filtered and the filtrate was evaporated to dryness. The residue was dissolved in dichloromethane (15 ml) and chromatographed on silica gel (Waters Prep 500 Instrument), eluting with a linear gradient of 2% ethanol in dichloromethane (4 l) and 8% ethanol in dichloromethane (4 l). Fractions containing the desired product were located by thin layer chromatography analysis, and these fractions were combined and were evaporated to dryness to yield 2.6 g of 6″-O-(tert-butyldimethylsilyl)-penta-N-CBZ-apramycin.

Step B: Preparation of 6″-O-(tert-butyldimethylsilyl)apramycin.

The 6″-O-(tert-butyldimethylsilyl)-penta-N-CBZ-apramycin from Step A (500 mg, 0.36 mmol) was dissolved in methanol (50 ml) and the solution was diluted with water (20 ml) and 0.1 N hydrochloric acid (5 ml) and then hydrogenated (1 atm $H_2$) over 5% palladium/carbon (500 mg) overnight at room temperature. The catalyst was removed by filtration and the filtrate was evaporated to dryness. The residue was dissolved in water (10 ml), the pH of this solution was adjusted to 9.3 with dilute ammonium hydroxide solution, and the mixture was loaded on a column of BioRex 70 (50 ml, $NH_4^+$ cycle, pH 9.3). The column was eluted with a linear gradient of 0.01 N ammonium hydroxide solution (500 ml) and 0.15 N ammonium hydroxide solution (500 ml). Fractions containing the desired product were located by thin layer chromatography analysis, and these fractions were combined and lyophilized to yield 97 mg of 6″-O-(tert-butyldimethylsilyl)apramycin: C-13 n.m.r. ($H_2O$-$D_2O$, pH 9-11) $\delta$ -5.0, 18.8, 26.5, 32.9, 33.1, 36.0, 49.9, 50.4, 51.3, 53.7, 62.3, 64.1, 66.2, 67.8, 71.1, 71.9, 73.5, 74.4, 76.8, 77.8, 87.4, 95.0, 96.2, 101.3.

Method 2

Penta-N-CBZ-apramycin (600 mg, 0.5 mmol) was dissolved in pyridine (25 ml) and 15 ml of solvent from this solution was distilled. The remaining solution was cooled to room temperature, treated with t-butyldimethylsilyl chloride (300 mg, 2 mmol), and warmed to 35° C. After stirring 3 h at 35° C., the reaction mixture was worked up as described in Method 1.

EXAMPLE 13

6″-Chloro-6″-Deoxyapramycin

Step A: Preparation of 6″-chloro-6″-deoxy-penta-N-CBZ-apramycin.

Penta-N-CBZ-apramycin (1.5 g, 1.24 mmol) was dissolved in pyridine (70 ml) and a strictly anhydrous solution was prepared by distilling 45 ml of solvent from this solution. The remaining solution was cooled in an ice bath and treated with triphenylphosphine (830 mg, 3.12 mmol) and N-chlorosuccinimide (418 mg, 3.12 mmol). The resultant brown solution was stirred overnight at room temperature and then quenched with methanol (4 ml) and evaporated to dryness. The remaining residue was dissolved in dichloromethane (140 ml) and extracted sequentially with 1 N hydrochloric acid (2×35 ml), 5% sodium bicarbonate solution (30 ml) and saturated sodium chloride solution (30 ml); the organic layer was dried over sodium sulfate and filtered and the filtrate was evaporated to dryness. The residue was triturated with ether (4×30 ml) and the insoluble product was collected by filtration to yield 1.22 g of crude 6″-chloro-6″-deoxy-penta-N-CBZ-apramycin.

Step B: Preparation of 6″-chloro-6″-deoxyapramycin.

The 6″-chloro-6″-deoxy-penta-N-CBZ-apramycin from Step A (1.0 g) was dissolved in ethanol (50 ml) and water (25 ml) and hydrogenated (1 atm $H_2$) over 5% palladium/carbon (1 g) at room temperature overnight. The catalyst was removed by filtration and the filtrate was concentrated to aqueous, filtered again and lyophilized. The residue was dissolved in water (10 ml), the pH of the solution was adjusted to 9.4 with aqueous sodium hydroxide solution and this product solution was loaded on a column of BioRex 70 (40 ml, pH 9.4). After briefly eluting with 0.01 N ammonium hydroxide solution, the column was eluted with a linear gradient of 0.01 N ammonium hydroxide solution (500 ml) and 0.1 N ammonium hydroxide solution (500 ml). Fractions containing the desired product were located by thin layer chromatography analysis, and these fractions were combined and lyophilized to yield 227 mg. of 6″-chloro-6″-deoxyapramycin. C-13 n.m.r. ($H_2O$-$D_2O$, pH 9–11) δ32.9, 33.0, 36.6, 45.6, 49.9, 50.4, 51.3, 54.2, 62.3, 66.2, 68.0, 71.0, 71.7, 73.2, 73.5, 76.9, 78.4, 87.7, 95.3, 96.5, 101.5; f.d.m.s. m/e=552 (P-17).

EXAMPLE 14

6″-Amino-6″-Deoxyapramycin

Step A: Preparation of 2″,3″;5,6-tetra-O-diisopropylidene-penta-N-CBZ-6″-O-(methanesulfonyl)apramycin.

2″,3″;5,6-Tetra-O-diisopropylidene-penta-N-CBZ-Apramycin (1.44 g, 1.11 mmol) dissolved in pyridine (30 ml) was treated at 0° C. with a solution of methanesulfonyl chloride (444 mg, 3.9 mmol) in cold pyridine (10 ml) as in Example 8 to yield the 6″-O-methanesulfonyl intermediate.

Step B: Preparation of 2″,3″;5,6-tetra-O-diisopropylidene-penta-N-CBZ-6″-azido-6″-deoxyapramycin.

The diisopropylidene-CBZ-6″-O-(methanesulfonyl)apramycin from Step A was dissolved in dimethylformamide (20 ml) and treated with a solution of lithium azide (550 mg, 11.1 mmol) in dimethylformamide (20 ml). After heating at 100° C. for 5.5 h, the solution was cooled and then added dropwise into water (100 ml). After stirring the resultant slurry for 0.25 h, the slurry was filtered and the precipitate was washed with water. The precipitate was dissolved in chloroform (80 ml) and extracted with 5% sodium bicarbonate solution (10 ml) and then water (10 ml). The chloroform layer was separated, dried over sodium sulfate and filtered and the filtrate was evaporated to dryness. The resultant residue was dissolved in chloroform (25 ml), diluted with cyclohexane (25 ml) and reevaporated to dryness to remove pyridine. The residue isolated was 2″,3″;5,6-diisopropylidene-penta-N-CBZ-6″-azido-6″-deoxyapramycin.

Step C: Preparation of penta-N-CBZ-6″-azido-6″-deoxyapramycin.

The diisopropylidene-CBZ-6″-azido-6″-deoxyapramycin from Step B was dissolved in cold trifluoroacetic acid (9 ml)-water (1 ml) and stirred for 1 h at 0° C. The solution was concentrated under reduced pressure, quenched with 5% sodium bicarbonate solution (15 ml) and extracted with chloroform (80 ml). The chloroform layer was extracted sequentially with 5% sodium bicarbonate solution and water and then dried over sodium sulfate. The dried solution was filtered and the filtrate was evaporated to dryness to yield penta-N-CBZ-6″-azido-6″-deoxyapramycin.

Step D: Preparation of 6″-amino-6″-deoxyapramycin.

The CBZ-6″-azido-6″-deoxyapramycin from Step C was dissolved in 2:1 ethanol:water (220 ml) and hydrogenated (1 atm $H_2$) over 5% palladium/carbon (equal weight) for 5.5 h at room temperature. The catalyst was removed by filtration and the filtrate was evaporated to dryness. The residue was dissolved in water (8 ml) and loaded on a column of BioRex 70 (30 ml, $NH_4^+$ cycle, pH 9.5). The column was eluted with water followed by a stepwise gradient using 100 ml volumes of dilute ammonium hydroxide solution (0.02 N to 0.08 N). The desired product was finally eluted with 0.1 N ammonium hydroxide solution; the appropriate fractions were combined and lyophilized to yield 153 mg of 6″-amino-6″-deoxyapramycin:

C-13 n.m.r. ($H_2O$-$D_2O$, pH 9–11) δ33.0 (×2), 36.7, 42.5, 49.9, 50.4, 51.3, 54.5, 62.4, 66.3, 68.0, 71.0, 71.8, 73.5, 74.3, 76.9, 78.6, 87.8, 95.1, 96.3, 101.6.

I claim:

1. A compound of the formula

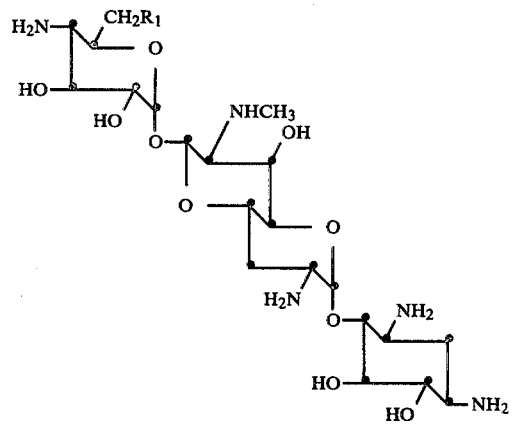

wherein $R_1$ is hydrogen, $C_1$ to $C_3$-alkylsulfonyloxy, phenylsulfonyloxy, substituted phenylsulfonyloxy, tert-butyldimethylsilyloxy, fluoro, chloro, bromo, iodo, azido, amino, $C_1$ to $C_3$-alkylthio, phenylthio, cyano or aminomethyl;

and the pharmaceutically acceptable acid addition salts thereof.

2. A compound of claim 1, wherein $R_1$ is hydrogen, $C_1$ to $C_3$-alkylsulfonyloxy, phenylsulfonyloxy, substituted phenylsulfonyloxy, tert-butyldimethylsilyloxy, fluoro, chloro, bromo, iodo or amino.

3. The compound of claim 2, wherein $R_1$ is hydrogen.

4. The compound of claim 2, wherein $R_1$ is p-toluenesulfonyloxy.

5. The compound of claim 2, wherein $R_1$ is methanesulfonyloxy.

6. The compound of claim 2, wherein $R_1$ is tert-butyldimethylsilyloxy.

7. The compound of claim 2, wherein $R_1$ is chloro.

8. The compound of claim 2, wherein $R_1$ is amino.

9. A compound of the formula:

[Structural formula: aminoglycoside with groups R3NH, CH2R2, O, CH3, N-R3, OH, R4, R'4, R3HN, NHR3, NHR3, R4, R'4]

wherein R$_2$ is C$_1$ to C$_3$-alkylsulfonyloxy, phenylsulfonyloxy, substituted phenylsulfonyloxy, azido, fluoro, bromo, iodo, C$_1$ to C$_3$-alkylthio, phenylthio or cyano, R$_3$ is benzyloxycarbonyl, C$_1$ to C$_4$ alkoxycarbonyl, trichloroethoxycarbonyl, formyl, trifluoroacetyl or phenoxycarbonyl and R$_4$ and R$_4'$ are both methyl, or taken together form a cyclohexyl ring.

10. A compound of claim 9, wherein R$_2$ is C$_1$ to C$_3$-alkylsulfonyloxy, p-toluenesulfonyloxy, azido, or iodo.

11. A compound of claim 10, wherein R$_2$ is methanesulfonyloxy, azido or iodo.

12. A compound of claim 9, wherein R$_3$ is benzyloxycarbonyl.

13. A compound of claim 9, wherein R$_4$ and R'$_4$ are each methyl.

14. A compound of claim 10 wherein R$_3$ is benzyloxycarbonyl.

15. A compound of claim 14, wherein R$_2$ is methanesulfonyl.

16. A compound of claim 14, wherein R$_2$ is azido.

17. A compound of claim 14, wherein R$_2$ is iodo.

18. The compounds of claims 15, 16 or 17, wherein R$_4$ and R$_4'$ are each methyl.

19. A compound of the formula

[Structural formula: aminoglycoside with groups R6NH, CH2OR5, O, CH3, N-R6, OH, R4, R'4, R6HN, NHR6, NHR6, R4, R'4]

wherein R$_4$ and R$_4'$ are the same and are methyl or are taken together to form a cyclohexyl ring, R$_5$ is chosen from the group consisting of hydrogen, a substituent of the formula $$\begin{array}{c} CH_3 \\ | \\ -C-OCH_3 \\ | \\ CH_3 \end{array}$$

or a substituent of the formula

[Structure: 6-membered ring with S and OCH$_3$ substituent]

and R$_6$ is chosen from the group consisting of benzyloxycarbonyl, trichloroethoxycarbonyl, formyl, trifluoroacetyl or phenoxycarbonyl; provided that, when R$_5$ is a substituent of the formula $$\begin{array}{c} CH_3 \\ | \\ -C-OCH_3 \\ | \\ CH_3 \end{array}$$

R$_4$ and R$_4'$ are methyl, and that, when R$_5$ is a substituent of the formula

[Structure: 6-membered ring with S and OCH$_3$ substituent]

R$_4$ and R$_4'$ are taken together to form a cyclohexyl ring.

20. A compound of claim 19, wherein R$_5$ is hydrogen.

21. A compound of claim 19, wherein R$_5$ is a group of the formula $$\begin{array}{c} CH_3 \\ | \\ -C-OCH_3. \\ | \\ CH_3 \end{array}$$

22. A compound of claim 20, wherein R$_6$ is benzyloxycarbonyl.

23. A compound of claim 21, wherein R$_6$ is benzyloxycarbonyl.

24. The compound of claims 22 or 23, wherein R$_4$ and R$_4'$ are each methyl.

25. A compound of the formula

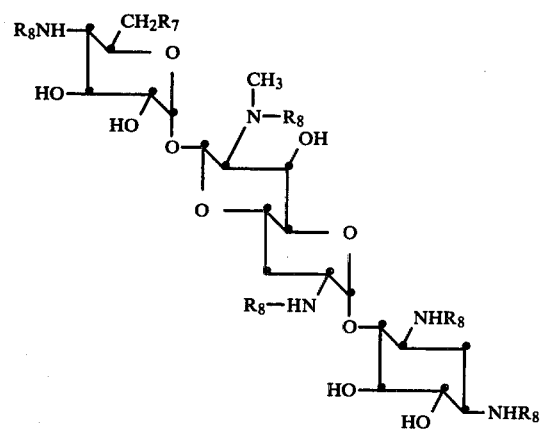

wherein $R_7$ is fluoro, chloro, bromo, iodo, cyano, $C_1$ to $C_3$-alkylsulfonyloxy, phenylsulfonyloxy, substituted phenylsulfonyloxy, azido, $C_1$ to $C_3$-alkylthio, phenylthio or tert-butyldimethylsilyloxy; and $R_8$ is benzyloxycarbonyl, $C_1$ to $C_4$-alkoxycarbonyl, trichloroethoxycarbonyl, formyl, trifluoroacetyl or phenoxycarbonyl.

26. A compound of claim 25, wherein $R_8$ is benzyloxycarbonyl.

27. A compound of claim 25, wherein $R_8$ is $C_1$ to $C_4$-alkoxycarbonyl.

28. A compound of claim 27, wherein $R_8$ is ethoxycarbonyl.

29. The compound of claim 26, wherein $R_7$ is methanesulfonyloxy.

30. The compound of claim 26, wherein $R_7$ is chloro.

31. The compound of claim 26, wherein $R_7$ is bromo.

32. The compound of claim 26, wherein $R_7$ is iodo.

33. The compound of claim 26, wherein $R_7$ is azido.

34. The compound of claim 26, wherein $R_7$ is p-toluenesulfonyloxy.

35. The compound of claim 26, wherein $R_7$ is tert-butyldimethylsilyloxy.

36. The compound of claim 28, wherein $R_7$ is p-toluenesulfonyloxy.

37. A compound of the formula

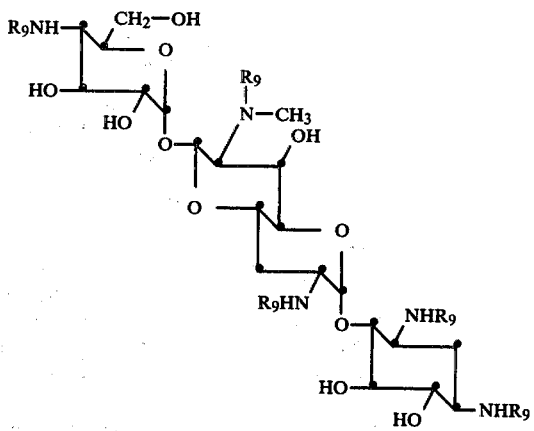

wherein $R_9$ is benzyloxycarbonyl, trichloroethoxycarbonyl, formyl, trifluoroacetyl or phenoxycarbonyl.

38. The compound of claim 37, wherein $R_9$ is benzyloxycarbonyl.

39. The compound of claim 37, wherein $R_9$ is formyl.

* * * * *